United States Patent
Tabata et al.

(10) Patent No.: US 9,352,053 B2
(45) Date of Patent: May 31, 2016

(54) PARTICLE AND PHOTOACOUSTIC CONTRAST AGENT HAVING THE PARTICLE

(71) Applicant: CANON KABUSHIKI KAISHA, Tokyo (JP)

(72) Inventors: Yasuhiko Tabata, Kyoto (JP); Sachiko Yamauchi, Yokohama (JP); Mayuko Kishi, Machida (JP); Masato Minami, Kawasaki (JP); Mika Yamagata, Tokyo (JP); Satoshi Yuasa, Yokohama (JP); Tetsuya Yano, Kyoto (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 240 days.

(21) Appl. No.: 13/926,666

(22) Filed: Jun. 25, 2013

(65) Prior Publication Data

US 2014/0017171 A1    Jan. 16, 2014

(30) Foreign Application Priority Data

Jul. 10, 2012 (JP) ................. 2012-154471
Mar. 4, 2013 (JP) ................. 2013-041919

(51) Int. Cl.
*A61K 49/00* (2006.01)

(52) U.S. Cl.
CPC ............ *A61K 49/00* (2013.01); *A61K 49/0021* (2013.01); *A61K 49/0093* (2013.01)

(58) Field of Classification Search
USPC ........................................ 424/9.1
See application file for complete search history.

(56) References Cited

U.S. PATENT DOCUMENTS

| 6,146,615 A | 11/2000 | Davies et al. |
| 6,423,296 B1 * | 7/2002 | Gunther et al. ............ 424/9.322 |
| 2011/0014125 A1 | 1/2011 | Bossmann et al. |
| 2011/0117023 A1 * | 5/2011 | Yamauchi .............. A61K 41/00 424/9.1 |
| 2011/0137235 A1 | 6/2011 | Kanehira et al. |
| 2012/0157824 A1 | 6/2012 | Bossmann et al. |

OTHER PUBLICATIONS

Martin P. Mienkina et al., "Evaluation of Ferucarbotran (Resovist®) as a Photoacoustic Contrast Agent," 54 Biomed. Tech. 83-88 (Mar. 2009).
Martin P. Mienkina et al., "Experimental Characterization of Ferucarbotran (Resovist®) as a Photoacoustic Nanoparticle Contrast Agent," 2006 IEEE Ultrasonics Symposium, p. 393-396 (2006).
Chulhong Kim et al., "In Vivo Photoacoustic Tomography of Chemicals: High-Resolution Functional and Molecular Optical Imaging at New Depths," 110(5) Chem. Rev. 2756-2782 (Mar. 2010).
T. Rajh et al., "Surface Restructuring of Nanoparticles: An Efficient Route for Ligand-Metal Oxide Crosstalk," 106(41) J. Phys. Chem. B pp. 10543-10552 (Sep. 2002).
Michael D. Shultz et al., "Reactive Nature of Dopamine as a Surface Functionalization Agent in Iron Oxide Nanoparticles," 129(9) J. Am. Chem. Soc. 2482-2487 (Feb. 2007).

* cited by examiner

*Primary Examiner* — Michael G Hartley
*Assistant Examiner* — Robert Cabral
(74) *Attorney, Agent, or Firm* — Fitzpatrick, Cella, Harper & Scinto (57) ABSTRACT

An iron oxide particle constituting a Resovist (trademark) absorbs a small quantity of light in a near infrared region and emits a weak photoacoustic signal. According to a particle having a catechol-like compound and iron atoms, the particle having a ratio of the number of moles of the catechol-like compound to the number of moles of the iron atoms of 270/10,000 or more, light absorption in the near infrared region increases and a strong photoacoustic signal can be transmitted.

10 Claims, 4 Drawing Sheets

BLOOD ONLY   PARTICLE A-10   BLOOD + PARTICLE A-10

FIG. 6D

PARTICLE AND PHOTOACOUSTIC CONTRAST AGENT HAVING THE PARTICLE

BACKGROUND OF THE INVENTION

1. Field of the Invention

The present invention relates to a particle and a photoacoustic imaging method using the particle.

2. Description of the Related Art

A photoacoustic imaging method of visualizing in vivo information has been known. The photoacoustic imaging method is a method involving measuring the intensity and generation position of a photoacoustic signal, which is emitted from a specimen through the irradiation of the specimen with light, to obtain the image of a substance distribution in the specimen. The light with which the specimen is irradiated is preferably near infrared light as light having a wavelength of 700 to 900 nm that easily permeates a living body.

It has been known that the irradiation of a Resovist (trademark) (contrast agent for MRI containing an iron oxide particle) with light produces an acoustic wave (2006 IEEE Ultrasonics Symposium p. 393-396). Therefore, there is a possibility that the Resovist (trademark) can be used as a contrast agent for photoacoustic imaging.

Here, the contrast agent for photoacoustic imaging refers to a contrast agent to be used in the photoacoustic imaging method. The photoacoustic imaging method refers to a method involving measuring the intensity and generation position of an acoustic wave, which is emitted from a specimen such as a living body through the irradiation of the specimen with light, to obtain the image of a substance distribution in the specimen. In the case where the contrast agent for photoacoustic imaging is liable to accumulate in a specific target site in the specimen, when an image is obtained by the photoacoustic imaging method after the specimen has been provided with the contrast agent for photoacoustic imaging, a contrast between the specific target site and any other site in the image increases.

However, the iron oxide particle constituting the Resovist (trademark) absorbs a small quantity of light in a near infrared region and emits a weak photoacoustic signal.

SUMMARY OF THE INVENTION

According to the present invention, there is provided a particle, including: a catechol-like compound; and iron atoms, in which the particle has a ratio of the number of moles of the catechol-like compound to the number of moles of the iron atoms of 270/10,000 or more. According to the present invention, it is possible to provide the particle that absorbs an increased quantity of light in the near infrared region and that transmits a strong photoacoustic signal.

Further features of the present invention will become apparent from the following description of exemplary embodiments with reference to the attached drawings.

DESCRIPTION OF THE EMBODIMENTS

A particle according to the present invention is a particle having a catechol-like compound and iron atoms, and has a ratio of the number of moles of the catechol-like compound to the number of moles of the iron atoms of 270/10,000 or more.

When photoacoustic imaging is performed by using a particle as a contrast agent, a photoacoustic signal sufficiently large as compared with a photoacoustic signal output from a living body needs to be output from the particle. On the other hand, not any kind of particle can be administered into the living body. Further, it is difficult to accumulate all of the administered particles in a site which one wishes to contrast. In view of the foregoing, it is desired to obtain a stronger photoacoustic signal with a smaller administration amount by increasing a light absorption quantity per particle.

Calculation was performed as described below based on a track record of the imaging of a lymph node of a mouse. While the light absorption quantity of a biological tissue is 0.05 cm$^{-1}$, an extra 0.1 cm$^{-1}$ in terms of a light absorption quantity is needed for achieving a sufficient contrast. The amount of particles that can be administered to one mouse is calculated to be $1.6 \times 10^{-7}$ mol in terms of the amount of Fe, from the administration amount of a Resovist (trademark) in terms of an Fe amount, i.e., 0.45 mg/kg, the average body weight of mice, i.e., 20 g, and the atomic weight of iron, i.e., 55.85. A ratio of particles that accumulated in the lymph node to the administered particles was 1 ID % on average. In other words, the amount of the particles that accumulate in the lymph node is $1.6 \times 10^{-9}$ mol in terms of an Fe amount. Since the average volume of the lymph nodes of a mouse is $9.4 \times 10^{-6}$ l, the concentration of the particles in the lymph node is $1.7 \times 10^{-4}$ mol/l in terms of an Fe concentration. In order that an extra 0.1 cm$^{-1}$ in terms of a light absorption quantity may be obtained through the accumulation of the particles at the concentration, the particles are each required to have a molar absorption coefficient $\epsilon$(Fe) per iron amount of 580 or more. The ratio of the number of moles of the molecules of the catechol-like compound to the number of moles of Fe needed for achieving an $\epsilon$(Fe) of 580 or more was estimated to be 270/10,000 or more. Performance required for each of the particles may be the same in a human being because his or her body weight simultaneously increases as his or her volume increases.

In the particle of the present invention, the iron atoms may each be present as an iron ion $Fe^{2+}$ or $Fe^{3+}$ in the particle. The term "iron atom" as used herein represents a concept comprehending atomic iron and an iron ion.

(Fe and O)

The particle of the present invention may contain iron atoms (Fe) and oxygen atoms (O). Examples of such particle include particles each containing, for example, $Fe_3O_4$ or $\gamma\text{-}Fe_2O_3$ in which an iron atom and an oxygen atom are bonded to each other, or a mixture thereof.

(Catechol-Like Compound)

The term "catechol-like compound" as used herein refers to the following compound. The compound has a benzene ring, one carbon atom out of the six carbon atoms of the benzene ring is substituted with a hydroxyl group, and the carbon atom at the ortho position viewed from the hydroxyl group is also substituted with a hydroxyl group (the following formula (1)). It should be noted that a carbon atom except the two carbon atoms having the hydroxyl groups in the catechol-like compound in the specification may also be substituted with a hydroxyl group or any other functional group.

(1)

(X represents a substituted or unsubstituted alkyl group having 1 to 10 carbon atoms and the substituent is an alkyl group having 1 to 5 carbon atoms, a hydroxyl group, an amino group, a carboxyl group, a phenyl group, or the like.)

Examples of the catechol-like compounds according to this embodiment may include catechol-like compounds such as dopamine (the following formula (2)), benserazide (the following formula (3)), adrenaline (the following formula (4)), isoprenaline (the following formula (5)), dobutamine (the following formula (6)), noradrenaline (the following formula (7)), levodopa (the following formula (8)), trimetoquinol (the following formula (9)), entacapone (the following formula (10)), droxidopa (the following formula (11), methyldopa (the following formula (12)), carbidopa (the following formula (13)), rutin (the following formula (14)), and tannic acid (the following formula (15)).

It should be noted that when enantiomers exist for the following compounds, both the following compounds and enantiomers thereof are included in the category of the catechol-like compound according to this embodiment.

-continued

-continued

In the present invention, the iron ions and the catechol-like compound may form a complex. The complex of the iron ions and the catechol-like compound has, in a near infrared wavelength region, an absorption peak in association with charge transfer transition from catechol to an iron ion. Consequently, the particle can absorb an additionally large quantity of light in the near infrared region, which is light having a wavelength of 700 to 900 nm that easily permeates a living body, to transmit a photoacoustic signal.

(Amorphous)

In general, iron-based particles can be classified into a crystalline particle and an amorphous particle. Those particles can be distinguished from each other depending on whether a diffracted intensity peak showing crystallinity is observed at a specific analysis angle when analysis is performed by an X-ray diffraction method. The term "amorphous" as used herein refers to a state where no peak showing crystallinity is observed when the particle is analyzed by the X-ray diffraction method.

The particle of the present invention may be crystalline or may be amorphous as long as the ratio of the number of moles of the molecules of the catechol-like compound to the number of moles of Fe satisfies the requirement. In general, when values each obtained by dividing a normalized photoacoustic signal PA(Fe) of a particle per iron amount by its molar absorption coefficient $\epsilon(Fe)$ per iron amount (hereinafter referred to as "signal conversion efficiency") are compared, the signal conversion efficiency of an amorphous particle is higher than that of a crystalline particle. In other words, the amorphous particle can output a stronger photoacoustic signal than that of the crystalline particle when the particles absorbed the same quantity of light. In addition, as the content of the catechol-like compound increases, there is a high possibility that the crystalline state of a particle collapses and hence the particle becomes amorphous. Consequently, the particle of the present invention is preferably amorphous.

(Particle Size)

The term "particle size" as used herein means the hydrodynamic diameter of a particle measured with a dynamic light scattering analyzer by a dynamic light scattering method. The average particle size of the particle according to this embodiment is preferably 1 nm or more and 5,000 nm or less. The average particle size is preferably nm or more because the particle having such average particle size is hardly excreted by a kidney, and is more preferably 1,000 nm or less because an enhanced permeability and retention (EPR) effect can be expected.

A particle having a desired average particle size can be produced by changing a production condition.

(Production Method)

The particle of the present invention can be produced by, for example, the following coprecipitation method. Although the coprecipitation method is described below, the method is merely a nonlimitative example and a method of producing the particle according to the present invention is not limited thereto.

When the coprecipitation method is employed, specifically, the particle of the present invention can be obtained by performing the following steps (1) to (3) in the stated order:

(1) the step of blending an aqueous solution containing iron ions and an aqueous solution containing a catechol-like compound to provide an aqueous solution containing the iron ions and the catechol-like compound;

(2) the step of adding a base to the aqueous solution containing the iron ions and the catechol-like compound to form the solution into particles; and (3) the step of removing, from the aqueous solution, the iron ions and catechol-like compound that have not been formed into particles.

(Deoxidation)

In order that the oxidation of, for example, an $Fe^{2+}$ ion may be prevented, dissolved oxygen in water to be used in the production may be removed by subjecting the water to nitrogen bubbling in advance. Alternatively, the steps (1) to (3) may be performed under a nitrogen atmosphere.

(Aqueous Solution Containing Fe)

The aqueous solution containing the iron ions contains the iron ions at a ratio "$Fe^{2+}:Fe^{3+}$" of 0:100 to 100:0 at the stage before the blending with the aqueous solution containing the catechol-like compound. The ratio "$Fe^{2+}:Fe^{3+}$" between $Fe^{2+}$ and $Fe^{3+}$ is more preferably, but not limited to, 36:64 to 0:100. It should be noted that the ratio is a ratio "$Fe^{2+}:Fe^{3+}$" in the aqueous solution and a ratio "$Fe^{2+}:Fe^{3+}$" in a particle to be obtained is not required to fall within the range. $Fe^{2+}$ is obtained by dissolving $FeCl_2$ or the like in water, or by causing $Fe^{3+}$ and the catechol-like compound to coexist. $Fe^{3+}$ is obtained by dissolving $FeCl_3$ or the like in water, or by oxidizing $Fe^{2+}$ with oxygen or the like.

(Base)

In the step (2), ammonia, methylamine, sodium hydroxide, lithium hydroxide, potassium hydroxide, or the like can be added as the base. The kind of the base is not limited to the foregoing as long as the addition of the base can produce a core that leads to the particle formation.

It has been generally known that an optimum pH upon production of an iron oxide particle is 8 to 14. Here, when the amount of iron ions that form the complex with the catechol-like compound is larger than the amount of iron ions that form iron oxide, a larger amount of the catechol-like compound can be incorporated. Consequently, the pH of the aqueous solution to be used upon preparation of the particle is preferably 7 or less, which is lower than the foregoing pH, and the pH is more preferably 5 or less.

(Temperature in Step of Particle Formation)

In general, upon production of an iron oxide particle, the aqueous solution to be used in the production of the particle is often warmed to 60 to 80° C. Here, when the amount of the iron ions that form the complex with the catechol-like compound is larger than the amount of the iron ions that form iron oxide, a larger amount of the catechol-like compound can be incorporated. Consequently, the temperature of the aqueous solution to be used upon preparation of the particle is preferably less than 60° C., which is lower than the foregoing temperature, and the temperature is more preferably 25° C. or less. In addition, when the particle formation is performed in the aqueous solution, the temperature of the aqueous solution is preferably 0° C. or more in order that water may be prevented from freezing.

(Acid)

An acid may be added to the aqueous solution between the steps (2) and (3) for the purpose of increasing the light absorption quantity or photoacoustic signal of the particle. In this embodiment, hydrochloric acid, nitric acid, or the like may be added, but the acid is not limited to the foregoing acids as long as the light absorption quantity or photoacoustic signal of the particle is increased.

(Removal)

A method of removing the iron ions and catechol-like compound that have not been formed into particles from the aqueous solution in the step (3) is, for example, dialysis, ultrafiltration, or centrifuge refining.

(Dispersion Stabilizer)

A dispersion stabilizer may be incorporated into the particle in the present invention for improving the dispersion stability of the particle in water.

As the dispersion stabilizer according to this embodiment, there may be used: a sugar such as a polysaccharide, a tetrasaccharide, a trisaccharide, a disaccharide, or a monosaccharide; a derivative of a sugar such as a sugar alcohol or a sugar acid; or polyethylene glycol (PEG) or a derivative of PEG such as aminated PEG.

For example, as the polysaccharide, there may be used a dextran, a carboxydextran, an aminated dextran, a dextrin, a sodium hyaluronate, a pullulan, an alginic acid, a pectin, an amylopectin, a glycogen, a cellulose, an agarose, an amylose, a carrageenan, a heparin sodium, a xyloglucan, a xanthan gum, or a hydroxypropyl cellulose.

As the tetrasaccharide, there may be used acarbose or stachyose.

As the trisaccharide, there may be used raffinose, melezitose, or maltotriose.

As the disaccharide, there may be used trehalose, sucrose, lactose, maltose, turanose, or cellobiose.

As the monosaccharide, there may be used dihydroxyacetone, glyceraldehyde, erythrulose, erythrulose, threose, ribulose, xylulose, xylose, lyxose, deoxyribose, psicose, fructose, sorbose, tagatose, glucose, mannose, gulose, galactose, talose, fucose, rhamnose, or sedoheptulose.

As the sugar derivative such as the sugar alcohol or the sugar acid, there may be used xylitol, inositol, calcium gluconate, sodium gluconate, magnesium gluconate, sorbitol, calcium saccharate, mannitol, or meglumine.

The particle of the present invention preferably has, as the dispersion stabilizer, at least one kind of a dextran, a carboxydextran, an aminated dextran, a pullulan, and a polyethylene glycol (PEG) out of those dispersion stabilizers.

The dispersion stabilizer may be added to the aqueous solution between the steps (1) and (2) of the production method or between the steps (2) and (3) of the production method.

(Contrast Agent for Photoacoustic Imaging)

A photoacoustic contrast agent in this embodiment is as follows. In this embodiment, the term "photoacoustic imaging" refers to the performance of imaging through the detection of an acoustic wave (photoacoustic signal) emitted from an object irradiated with light. The use of the particle according to this embodiment as a contrast agent (photoacoustic contrast agent) can reinforce the acoustic wave from the object to enable the photoacoustic imaging with a strong contrast because the particle absorbs a large quantity of light to emit an additionally strong acoustic wave. It should be noted that the photoacoustic imaging is a concept comprehending photoacoustic tomography.

The photoacoustic contrast agent according to this embodiment may further have a dispersion medium such as physiological saline, distilled water for injection, or phosphate buffered physiological saline. In addition, the photoacoustic contrast agent according to this embodiment may have a pharmacologically acceptable additive as required. The photoacoustic contrast agent according to this embodiment may be dispersed in the dispersion medium in advance or may be used as: the contrast agent is prepared as a kit and is then dispersed in the dispersion medium before administration into a living body.

When administered into a living body, the photoacoustic contrast agent according to this embodiment can be accumulated in a larger amount in a tumor site than that in a normal site in the living body by utilizing the EPR effect. As a result, when an acoustic wave from the living body is detected through the irradiation of the living body with light after the particle has been administered into the living body, an acoustic wave emitted from the tumor site can be enlarged as compared with an acoustic wave emitted from the normal site. Therefore, the particle according to this embodiment can be used as a photoacoustic contrast agent for specifically detecting a tumor site.

(Contrasting Method)

A method of detecting a photoacoustic signal from the particle according to this embodiment administered into a living body, the particle being used as a contrast agent, with a photoacoustic imaging apparatus includes the following steps, provided that the contrasting method according to this embodiment may include a step except the following steps:
(a) the step of administering the particle according to this embodiment into the living body; and
(b) the step of irradiating the living body with light to detect the photoacoustic signal emitted from the particle according to this embodiment present in the living body.

Re: (a)

A method of administering the particle according to this embodiment into the living body is not particularly limited, and a method such as oral administration, intravenous injection, or subcutaneous injection can be adopted. The particle according to this embodiment can efficiently detect a tumor because the particle can be accumulated in the tumor by the EPR effect.

Re: (b)

The light with which the living body is irradiated is preferably light having a near infrared wavelength of 600 nm to 900 nm because the light is safe when applied to the living body and shows high body permeability. An apparatus for generating the light and an apparatus for detecting the acoustic signal are not particularly limited, and various apparatus can be used. The contrasting method involving using the particle according to this embodiment can contrast a site such as a tumor through the steps (a) and (b).

Hereinafter, the present invention is described in more detail by way of examples. However, the present invention is not limited to these examples, and a material, a composition condition, a reaction condition, and the like can be freely changed to such an extent that a particle having the same function and effect is obtained.

The particles of the present invention produced as examples are hereinafter referred to as A-1, A-2, A-3, and the like, and particles produced as comparative examples are hereinafter referred to as B-1, B-2, B-3, and the like.

As described later, the particles produced as the examples each satisfied the condition that a ratio "catechol/Fe" should be 270/10,000 or more under which photoacoustic imaging was able to be performed, but none of the particles produced as the comparative examples satisfied the condition.

Example 1

Comparative Example 1

An amorphous particle containing dopamine represented by the formula (2) as a catechol-like compound and a pullulan as a dispersion stabilizer (hereinafter referred to as "particle A-1") was produced by the following method. Further, the particle was compared with a crystalline particle (B-1) free of dopamine and an amorphous particle (B-2) free of dopamine.

Dissolved oxygen was removed by subjecting water to be used to nitrogen bubbling for 30 minutes in advance. 1.5 Milliliters ($3.1\times10^{-4}$ mol in terms of $Fe^{2+}$) of a 41-mg/ml aqueous solution of $FeCl_2.4H_2O$ and 1.5 ml ($5.6\times10^4$ mol in terms of $Fe^{3+}$) of a 100-mg/ml aqueous solution of $FeCl_2.6H_2O$ were charged into a three-necked flask containing 11.6 ml of water. The aqueous solution containing $Fe^{2+}$ and $Fe^{3+}$ was mixed at a speed of 200 rpm under a nitrogen atmosphere while being warmed at 80° C. with an oil bath. 1.14 Milliliters (3-hydroxytyramine hydrochloride, $6.0\times10^{-4}$ mol in terms of dopamine) of a 100-mg/ml aqueous solution of dopamine were added to the aqueous solution containing $Fe^{2+}$ and $Fe^{3+}$, and then the mixing and the warming were continued for 15 minutes under the nitrogen atmosphere. The warming was stopped and then the mixing was continued for 5 minutes under the nitrogen atmosphere. Next, 2.4 ml of a 0.5-mol/l aqueous solution of NaOH and 12.7 ml of a 20-mg/ml aqueous solution of a pullulan were added to the aqueous solution, and then the mixing was continued for 2 hours under the nitrogen atmosphere to form the resultant aqueous solution into particles.

500 Microliters of a 1-mol/l aqueous solution of HCl were added to the aqueous solution and then the resultant aqueous solution was mixed. After that, Fe, dopamine, and the pullulan that had not been formed into particles were removed from the aqueous solution that had been formed into particles by performing dialysis with a dialysis membrane having a pore size of 50 kDa and performing ultrafiltration with an Amicon Ultra-4 (Japan Millipore) having a pore size of 100 kDa. The agglomerate was removed by filtration with a filter having a pore size of 1.2 μm. Thus, the particle A-1 was obtained.

For comparison, commercial iron oxide (Resovist (trademark)) was used as the crystalline particle (B-1) free of dopamine. The amorphous particle (B-2) free of dopamine was produced under the same conditions as those of the particle A-1 except that dopamine was not added.

The shape of a particle was observed with a transmission electron microscope (Hitachi, Ltd., H800) and the crystal structure of the particle was observed with an X-ray diffractometer (PANalytical, X'Pert PRO). At the time of the observation of the crystal structure, particles to be observed were dried before about 1 g thereof was used in the observation. When no peaks were observed in the results of the measurement with the X-ray diffractometer, the particles were judged to be amorphous.

Figure 1:
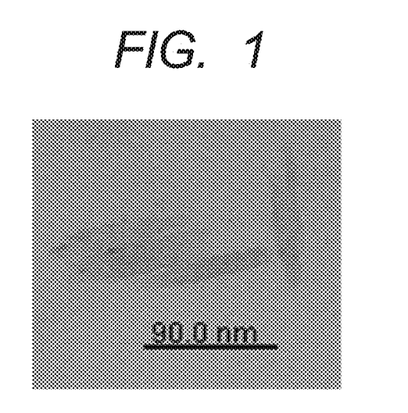
FIG. 1 is a transmission microphotograph of a particle.
Figure 2:
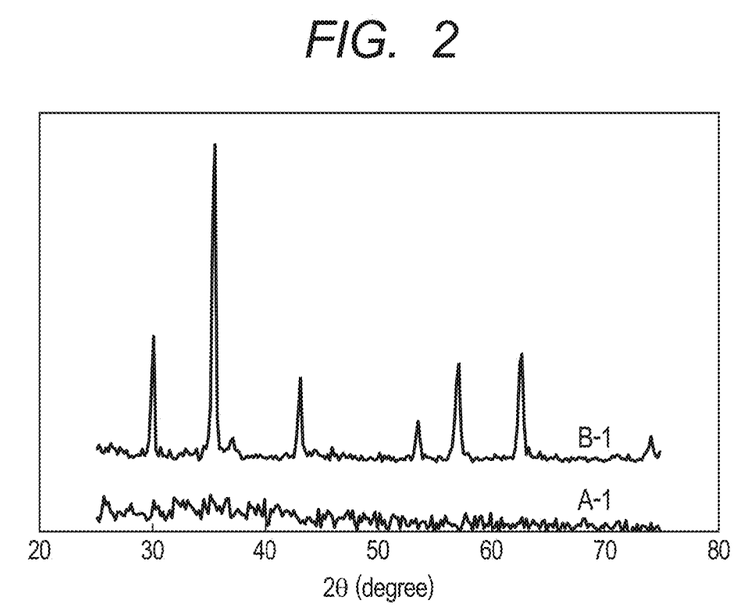
FIG. 2 shows the results of the measurement of X-ray diffraction.

FIG. 1 is a photograph obtained by observing the particle A-1 with the transmission electron microscope. The particle A-1 was of a rice-like shape. FIG. 2 shows the results of the measurement of the X-ray diffraction of each of the particles A-1 and B-2. The particle A-1 was an amorphous particle because the particle showed no specific peak.

The molar absorption coefficient $\epsilon(Fe)$ ($cm^{-1}M^{-1}$) of a particle per iron amount was determined by measuring its absorbance and Fe concentration. First, the absorbance was measured with a spectrophotometer (PerkinElmer, Inc., Lambda Bio40). Meanwhile, the particle was dissolved in concentrated nitric acid and then the Fe concentration was determined with an emission spectrometer (SPECTRO, CIROS CCD). The molar absorption coefficient $\epsilon(Fe)$ ($cm^{-1}M^{-1}$) was determined by dividing the absorbance by the molar concentration of Fe and a cell width.

Figure 3:
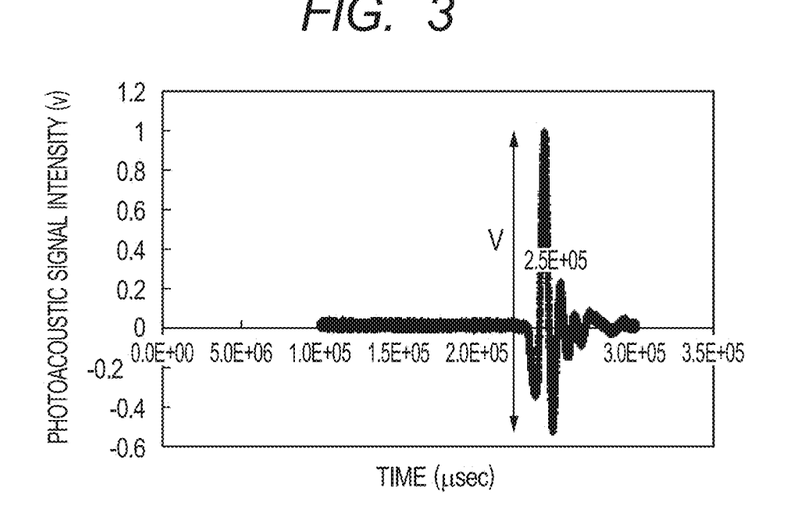
FIG. 3 shows the results of the measurement of a photoacoustic signal intensity.

The measurement of a photoacoustic signal was performed by: irradiating a particle dispersed in water with pulse laser light; detecting the photoacoustic signal from the particle with a piezoelectric element; amplifying the signal with a high-speed preamplifier; and then acquiring its waveform with a digital oscilloscope. Specific conditions are as described below. Titanium sapphire laser (Lotis, LT-2211-PC) was used as a pulse laser light source. A wavelength was set to 710, 750, 800, and 850 nm, an energy density was set to 20 to 50 mJ/cm$^2$ (depending on the selected wavelength), a pulse width was set to about 20 nanoseconds, and a pulse repetition frequency was set to 10 Hz. A cuvette made of polystyrene having a width of 1 cm and an optical path length of 0.1 cm was used as a measuring container for storing the particle dispersed in water. An unfocused ultrasonic transducer (Panametrics-NDT, V303) having an element diameter of 1.27 cm and a central band of 1 MHz was used as the piezoelectric element for detecting the photoacoustic signal. The measuring container and the piezoelectric element were immersed in a glass container filled with water, and an interval therebetween was set to 2.5 cm. An ultrasonic preamplifier (Olympus Corporation, Model 5682) having an amplification degree of +30 dB was used as the high-speed preamplifier for amplifying the photoacoustic signal. The amplified signal was input in the digital oscilloscope (Tektronix, DPO4104). The cuvette made of polystyrene was irradiated with the pulse laser light from the outside of the glass container. Part of scattered light generated at that time was detected with a photodiode and then input as a trigger signal in the digital oscilloscope. The digital oscilloscope was set to a 32-run averaging display mode to acquire an average photoacoustic signal as a result of 32 times of laser pulse irradiation. FIG. 3 shows a typical waveform of the photoacoustic signal. As indicated by arrows in the figure, a photoacoustic signal intensity (V) was determined from the waveform. A value obtained by dividing the resultant photoacoustic signal intensity by the energy (J) of the applied pulse laser was defined as a normalized photoacoustic signal (VJ$^{-1}$). Further, a normalized photoacoustic signal PA(Fe) (VJ$^{-1}$M$^{-1}$) per iron amount was obtained by dividing the value by the Fe concentration.

A value obtained by dividing the normalized photoacoustic signal PA(Fe) per iron amount by the molar absorption coefficient ϵ(Fe) per iron amount was defined as signal conversion efficiency.

Table 1 summarizes the conditions for the production of the particles A-1, B-1, and B-2, and the results of the measurement of the particles. The table shows the molar absorption coefficient ϵ(Fe) per iron amount and normalized photoacoustic signal PA(Fe) per iron amount at a wavelength of 710 nm (the following tables also show results at a wavelength of 710 nm unless otherwise stated). The amorphous particles each showed higher signal conversion efficiency than that of the crystalline particle. Further, the light absorption quantity of the particle containing dopamine increased. In addition, the particle maintained high signal conversion efficiency and output a strong photoacoustic signal.

TABLE 1

|  |  | B-1 | B-2 | A-1 |
|---|---|---|---|---|
| Dopamine |  | x | x | ○ |
| State |  | Crystal | Amorphous | Amorphous |
| ϵ (Fe) | (cm$^{-1}$M$^{-1}$) | $1.9 \times 10^1$ | $3.7 \times 10^1$ | $5.0 \times 10^3$ |
| PA (Fe) | (VJ$^{-1}$M$^{-1}$) | $3.1 \times 10^2$ | $1.2 \times 10^3$ | $1.6 \times 10^5$ |
| Signal conversion efficiency |  | 17 | 32 | 32 |

Example 2

Comparative Example 2

Amorphous particles A-2 to A-5 each containing dopamine as a catechol-like compound and a dextran as a dispersion stabilizer were produced by the following method. For comparison, a particle B-3 free of dopamine was also produced.

240 Microliters ($5.0 \times 10^{-5}$ mol in terms of Fe$^{2+}$) of a 41-mg/ml aqueous solution of FeCl$_2$.4H$_2$O and 240 μl ($8.9 \times 10^{-5}$ mol in terms of Fe$^{3+}$) of a 100-mg/ml aqueous solution of FeCl$_2$.6H$_2$O were charged into a 30-ml glass bottle containing 2.32 ml of water to provide an aqueous solution containing Fe$^{2+}$ and Fe$^{3+}$. An aqueous solution containing Fe and dopamine was obtained by adding a 100-mg/ml aqueous solution of dopamine (whose amount in terms of dopamine had been regulated so as to be $9.5 \times 10^{-5}$, $4.7 \times 10^{-4}$, $9.5 \times 10^{-4}$, or $1.9 \times 10^{-3}$ mol) while mixing the aqueous solution containing Fe$^{2+}$ and Fe$^{3+}$ at a speed of 100 rpm. 384 Microliters ($1.9 \times 10^{-4}$ mol) of a 0.5-mol/l aqueous solution of NaOH and 2 ml of a 20-mg/ml aqueous solution of a dextran (dextran 40, molecular weight: about 40,000) were added to the aqueous solution of Fe and dopamine. The resultant aqueous solution was formed into particles (A-2 to A-5) by being continuously mixed for 2 hours. The particle B-3 free of dopamine was produced by the same method as that of each of the particles A-2 to A-5 except that dopamine was not added.

The particle size of each of the particles was measured with a dynamic light scattering analyzer (Otsuka Electronics Co., Ltd., ELS-Z). A set of 100 times of integration was performed 5 times and then the particle size was determined by averaging the calculated 5 pieces of data. The normalized photoacoustic signal PA(Fe) per iron amount was measured in the same manner as in Example 1.

Table 2 summarizes the conditions for the production of the particles A-2 to A-5 and B-3, and the results of the measurement of the particles. A particle was able to be produced even when the dextran was used as a dispersant. The normalized photoacoustic signal PA(Fe) per iron amount was able to be changed by changing the amount of dopamine to be used at the time of the production. The amount of dopamine at the time of the production, i.e., $4.7 \times 10^{-4}$ mol corresponds to a 3.4-fold equivalent of the total Fe amount of Fe$^{2+}$ and Fe$^{3+}$ at the time of the production. Fe and dopamine can form a complex at a ratio of up to 1:3. Consequently, it is assumed that when the production was performed at $4.7 \times 10^{-4}$ mol (in other words, 3.4-fold equivalent) or more, the complex of Fe and dopamine was sufficiently formed, and as a result, values for the PA(Fe)'s of the resultant particles became substantially the same.

TABLE 2

|  |  | Particle ||||| 
|---|---|---|---|---|---|---|
|  |  | B-3 | A-2 | A-3 | A-4 | A-5 |
| Dopamine | (mol) | 0 | $9.5 \times 10^{-5}$ | $4.7 \times 10^{-4}$ | $9.5 \times 10^{-4}$ | $1.9 \times 10^{-3}$ |
| Particle size | (nm) | 330 | 29 | 114 | 350 | 2,089 |
| PA(Fe) | (VJ$^{-1}$M$^{-1}$) | $1.0 \times 10^2$ | $2.7 \times 10^4$ | $1.4 \times 10^5$ | $1.3 \times 10^5$ | $1.4 \times 10^5$ |

Example 3

An amorphous particle A-6 containing dopamine as a catechol-like compound and a dextran as a dispersion stabilizer was produced with only $Fe^{3+}$ as iron by the following method.

2.35 Milliliters ($8.7 \times 10^{-4}$ mol in terms of $Fe^{3+}$) of a 100-mg/ml aqueous solution of $FeCl_3 \cdot 6H_2O$ were charged into a three-necked flask containing 12.1 ml of water. The aqueous solution containing $Fe^{3+}$ was mixed at a speed of 200 rpm under a nitrogen atmosphere. 5.7 Milliliters ($3.0 \times 10^{-3}$ mol in terms of dopamine) of a 100-mg/ml aqueous solution of dopamine were added to the aqueous solution of $Fe^{3+}$. Next, 2.4 ml of a 0.5-mol/l aqueous solution of NaOH and 6.4 ml of a 40-mg/ml aqueous solution of the dextran were added to the aqueous solution, and then the mixing was continued for 2 hours under the nitrogen atmosphere to form the resultant aqueous solution into particles.

The particle size and the normalized photoacoustic signal PA(Fe) per iron amount were measured in the same manner as in Examples 1 and 2.

Table 3 summarizes the results of the measurement of the particle A-6. A particle was able to be produced even when only $Fe^{3+}$ was used as iron.

TABLE 3

|  |  | Particle A-6 |
|---|---|---|
| Particle size | (nm) | 173 |
| PA (Fe) | $(VJ^{-1}M^{-1})$ | $1.9 \times 10^5$ |

Example 4

An amorphous particle A-7 containing dopamine as a catechol-like compound and a dextran as a dispersion stabilizer was produced by the following method, and then its accumulation property in a lymph node was confirmed.

240 Microliters ($5.0 \times 10^{-5}$ mol in terms of $Fe^{2+}$) of a 41-mg/ml aqueous solution of $FeCl_2 \cdot 4H_2O$ and 240 μl ($8.9 \times 10^{-5}$ mol in terms of $Fe^{3+}$) of a 100-mg/ml aqueous solution of $FeCl_3 \cdot 6H_2O$ were charged into a 30-ml glass bottle containing 2.32 ml of water to provide an aqueous solution containing $Fe^{2+}$ and $Fe^{3+}$. An aqueous solution containing Fe and dopamine was obtained by: adding 180 μl ($9.5 \times 10^{-5}$ mol in terms of dopamine) of a 100-mg/ml aqueous solution of dopamine while mixing the aqueous solution containing $Fe^{2+}$ and $Fe^{3+}$ at a speed of 100 rpm; and mixing the resultant for 25 minutes. 384 Microliters ($1.9 \times 10^{-4}$ mol) of a 0.5-mol/l aqueous solution of NaOH and 2 ml of a 20-mg/ml aqueous solution of the dextran were added to the aqueous solution of Fe and dopamine. The resultant aqueous solution was formed into particles by being continuously mixed for 2 hours.

The resultant particle A-7 was examined for its accumulation property in a lymph node of a mouse. 10 Microliters of an aqueous solution prepared by dispersing the particle at a concentration of 3.1 mg/ml in terms of an Fe concentration were subcutaneously injected into a planta portion of the mouse, and 24 hours after that, a lymph node of a lower limb was taken out. The lymph node was homogenized in a 1% Triton-X100 aqueous solution. Hydrochloric acid was added to the resultant and then the mixture was centrifuged to provide a supernatant in which the Fe ions had been extracted. The Fe concentration was determined by performing colorimetry with 2-nitroso-5-[N-n-propyl-N-(3-sulfopropyl) amino]phenol. An average of 1.3 ID % of the administered particles accumulated in the lymph node.

Comparative Example 3

Dopamine was caused to adsorb to a particle free of dopamine and then the resultant was compared with such a dopamine-containing particle that dopamine had been used at the time of the production of the particle.

The particle B-2 was used as the particle free of dopamine. A particle B-4 that had adsorbed dopamine was produced by causing dopamine to adsorb to the particle B-2. The particle A-1 was used as such dopamine-containing particle that dopamine had been used at the time of the production.

A method of causing dopamine to adsorb to the particle is as described below. An aqueous solution of dopamine was added to a dispersion aqueous solution of the particle B-2. The amount of dopamine at this time was adjusted so that a ratio between Fe in the particle and dopamine in the aqueous solution became 1.5:1 (mol:mol) (because a ratio between Fe and dopamine had been 1.5:1 at the time of the production of the particle A-1). Dialysis was performed for removing dopamine that had not adsorbed to the particle.

The light absorption quantity $\epsilon$(Fe) per iron amount and the normalized photoacoustic signal PA(Fe) per iron amount were measured in the same manner as in Example 1. In addition, on the assumption that contrasting would be performed by administering a particle into a living body, the particle was blended with a fetal bovine serum and then the blend was incubated at 37° C., followed by the measurement of an absorbance every fixed time. A change of the absorbance represents a value for the absorbance at each measuring time in the case where the absorbance before the initiation of the incubation is defined as 1.

Table 4 shows the results of the evaluations of the particle B-2 free of dopamine, the particle B-4 to which dopamine has been caused to adsorb, and the particle A-1 containing dopamine. As can be seen from the results of the particle B-2 free of dopamine and the particle B-4 to which dopamine had been caused to adsorb, the light absorption quantity and photoacoustic signal of a particle increased even when dopamine was caused to adsorb to the particle after its production. However, the light absorption quantity and photoacoustic signal of such particle that dopamine had been used at the time of the production like the particle A-1 containing dopamine increased to a much larger extent than those of the particle to which dopamine had been caused to adsorb did.

TABLE 4

|  |  | B-2 Particle free of dopamine | B-4 Particle to which dopamine has been caused to adsorb | A-1 Particle containing dopamine |
|---|---|---|---|---|
| $\epsilon$ (Fe) | $(cm^{-1}M^{-1})$ | $3.7 \times 10^1$ | $4.9 \times 10^1$ | $5.0 \times 10^2$ |
| PA (Fe) | $(VJ^{-1}M^{-1})$ | $1.2 \times 10^3$ | $1.5 \times 10^3$ | $1.1 \times 10^4$ |

Figure 4:
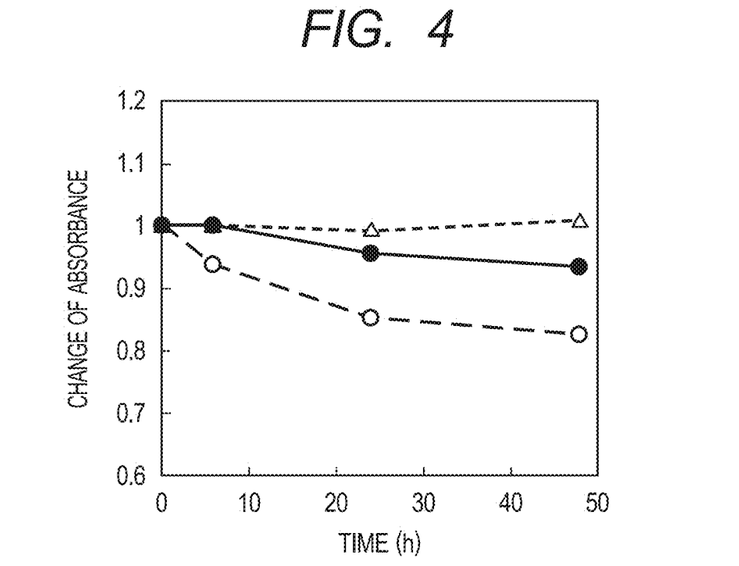
FIG. 4 is a graph showing the stability in a serum of each of a particle B-2 free of dopamine, a particle B-4 to which dopamine has been caused to adsorb, and a particle A-1 containing dopamine.

FIG. 4 shows the results of the measurement of the changes of the absorbances of the particle B-2 free of dopamine (white triangle), the particle B-4 to which dopamine has been caused to adsorb (white circle), and the particle A-1 containing dopamine (black circle). The changes of the absorbances of the particle B-4 to which dopamine had been caused to adsorb and the particle A-1 containing dopamine reduced as compared with that of the particle B-2 free of dopamine. It is assumed that dopamine changed as a result of the incubation in the serum at 37° C., and hence the coordination of dopamine and Fe changed. The change of the absorbance of the particle B-4 to which dopamine had been caused to adsorb showed a large change as compared with that of the particle A-1 containing dopamine. It is assumed that in the case of the particle B-4 to which dopamine had been caused to adsorb, dopamine was present on the surface of the particle and hence the denaturation of dopamine was easily caused by a component in the serum.

The particle containing dopamine absorbed a large quantity of light and output a strong photoacoustic signal as compared with the particle to which dopamine had been caused to adsorb. In addition, the former particle showed a small signal change when contrasting was performed by administering the particle into the living body. The particle of the present case was able to emit a photoacoustic signal more strongly and more stably than the particle to which dopamine had been caused to adsorb did.

Comparative Example 4

A particle (B-5) was produced by the following method for examining an influence of a pH in the step of particle formation on the PA(Fe) of a particle to be obtained.

As in the particle A-7, $Fe^{2+}$, $Fe^{3+}$, water, and dopamine were added, and then 600 μl ($3.0 \times 10^{-4}$ mol in terms of NaOH) of a 0.5-mol/l aqueous solution of NaOH were added to produce the particle B-5.

The pH of the resultant solution immediately after the addition of NaOH was measured with a pH meter (HORIBA, Ltd., B-212). The normalized photoacoustic signal PA(Fe) per iron amount was measured in the same manner as in Example 1. In addition, the Fe amount of the resultant particle was calculated from the Fe concentration and the liquid amount, and then an Fe yield was calculated from the amount of Fe used in the production.

Table 5 summarizes the condition for the production of the particle and the results of the measurement of the particle. The results of the particle A-7 were also shown for comparison. As the pH immediately after the addition of NaOH increased, i.e., the pH in the step of particle formation increased, the PA(Fe) of the resultant particle weakened and the Fe yield increased.

TABLE 5

|  |  | A-7 | B-5 |
|---|---|---|---|
| NaOH | (mol) | $1.9 \times 10^{-4}$ | $3.0 \times 10^{-4}$ |
| pH |  | 4.7 | 7.2 |
| PA (Fe) | ($VJ^{-1}M^{-1}$) | $4.6 \times 10^4$ | $8.6 \times 10^3$ |
| Fe yield | (%) | 6 | 50 |

It is probably because the Fe ions were formed into particles while sufficiently forming a complex with dopamine that the PA(Fe) strengthened. Meanwhile, it is probably because the Fe ions were used in the growth of iron oxide and then formed into particles that the Fe yield increased. The results showed that whether the Fe ions were used in the formation of the complex with dopamine or the Fe ions were used in the growth of iron oxide might be related to the pH at the time of the particle formation.

It has been generally known that when iron oxide particles are produced, an optimum pH in the step of particle formation is 8 to 14. Here, when the amount of the iron ions that form the complex with dopamine is larger than the amount of the iron ions that form iron oxide, a larger amount of dopamine can be incorporated and the PA(Fe) may be larger as the amount of dopamine increases. It is assumed that at a pH of 7.2, the formation of iron oxide became dominant over the formation of the iron complex and hence the PA(Fe) became small, and at a pH of 4.7, the formation of the iron complex became dominant over the formation of iron oxide and hence the PA(Fe) became large.

The pH for the particle formation needs to be more acidic than 7.2 for obtaining a particle outputting a stronger PA(Fe).

Example 5

Comparative Example 5

Particles (A-8 and B-6) were each produced by the following method for examining an influence of a temperature in the step of particle formation on the PA(Fe) of a particle to be obtained.

As in the particle A-2, $Fe^{2+}$, $Fe^{3+}$, and dopamine were added, and then NaOH was added. Further, a dextran was added to the mixture and then the whole was continuously mixed for 2 hours while being heated to 0 or 60° C. Thus, the particle A-8 or B-6 was produced.

The normalized photoacoustic signal PA(Fe) per iron amount was measured in the same manner as in Example 1. In addition, the Fe amount of each of the resultant particles was calculated from the Fe concentration and the liquid amount, and then an Fe yield was calculated from the amount of Fe used in the production.

Table 6 shows the measured results. The results of the particle A-2 were also shown for comparison. Heating in the step of particle formation reduced the PA(Fe) and increased the Fe yield. It is assumed that the heating promoted the growth of iron oxide.

In general, when iron oxide particles are produced, an aqueous solution to be used in particle production is often warmed to 60 to 80° C. in the step of particle formation. Here, when the amount of the iron ions that form the complex with dopamine is larger than the amount of the iron ions that form iron oxide, a larger amount of dopamine can be incorporated and the PA(Fe) may be larger as the amount of dopamine increases. It is assumed that in the case of each of the particles A-8 and A-2 formed at 0° C. and 25° C. (room temperature), the formation of the complex became dominant over the formation of iron oxide and hence the PA(Fe) strengthened, and in the case of the particle B-6 formed at 60° C., the formation of iron oxide became dominant over the formation of the complex and hence the PA(Fe) weakened.

Heating in the step of particle formation cannot provide a particle outputting a strong PA(Fe).

TABLE 6

|  |  | A-8 | A-2 | B-6 |
|---|---|---|---|---|
| Temperature for particle formation |  | 0° C. | 25° C. (room temperature) | 60° C. |
| PA (Fe) | ($VJ^{-1}M^{-1}$) | $2.1 \times 10^4$ | $2.7 \times 10^4$ | $1.3 \times 10^4$ |
| Fe yield | (%) | 9.6 | 13 | 27 |

Example 6

Comparative Example 6

The amount of dopamine in a particle and a photoacoustic signal were compared.

The amounts of dopamine in the particles (A-2 to A-7) of the present case, the particle (B-3) free of dopamine, the particle (B-4) to which dopamine had been caused to adsorb, the particle being prepared with reference to the Journal of the American Chemical Society 2007; 129: pp. 2482-2487, and the particle (B-6) formed by heating, the particle being prepared with reference to U.S. Pat. No. 6,146,615, were determined.

The amount of dopamine in each of the particles was determined by determining the amount of nitrogen atoms. First, the particle was freeze-dried. After that, the amount of the nitrogen atoms was determined with a trace nitrogen analyzer (Mitsubishi Chemical Corporation, ND-100) by an oxidative decomposition-vacuum emission method and defined as the amount of dopamine.

Figure 5A:
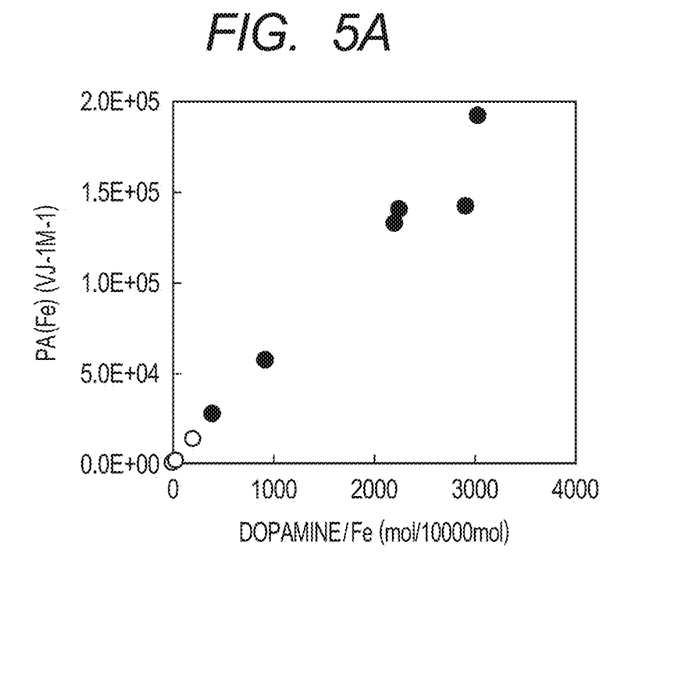
FIG. 5A and FIG. 5B are each a graph showing a relationship between dopamine and a photoacoustic signal.
Figure 5B:
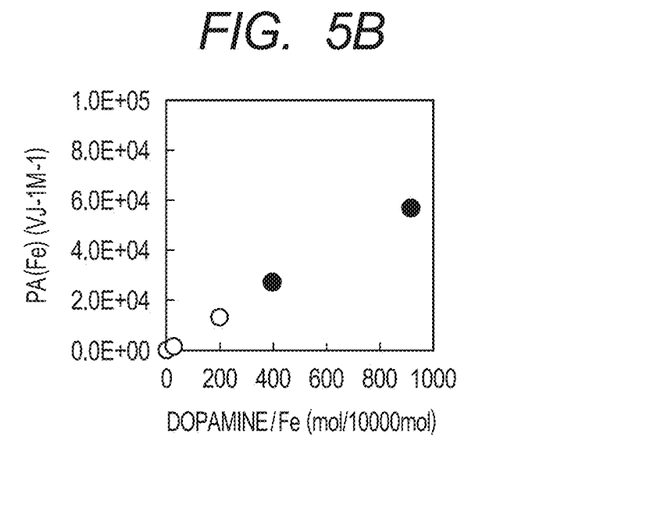

FIG. 5A and FIG. 5B are each a graph showing a relationship between the amount of dopamine in a particle and a photoacoustic signal. FIG. 5A shows the entire graph and FIG. 5B shows an enlarged view of part of the graph. The axis of abscissa indicates the number of moles of dopamine per 10,000 mol of Fe. The axis of ordinate indicates a photoacoustic signal per Fe atom. Black circles represent the results of the measurement of the particles A-2 to A-7. The photoacoustic signal strengthened in proportion to the amount of dopamine in the particle. White circles represent the results of the measurement of the particles B-3, B-4, and B-6. The photoacoustic signal was weak in each of the particles B-3, B-4, and B-6.

While the light absorption quantity of a biological tissue is 0.05 cm$^{-1}$, an extra 0.1 cm$^{-1}$ in terms of a light absorption quantity is needed for achieving a sufficient contrast. The amount of particles that can be administered to one mouse is $1.6 \times 10^{-7}$ mol in terms of an Fe amount because the administration amount of a Resovist (trademark) in terms of an Fe amount is 0.45 mg/kg, the average body weight of mice is 20 g, and the atomic weight of iron is 55.85. Example 4 showed that a ratio of particles that accumulated in a lymph node to the administered particles was about 1 ID %. In other words, the amount of the particles that accumulate in the lymph node is $1.6 \times 10^{-9}$ mol in terms of an Fe amount. Since the average volume of the lymph nodes of a mouse is $9.4 \times 10^{-6}$ l, the concentration of the particles in the lymph node is $1.7 \times 10^{-4}$ mol/l in terms of an Fe concentration. In order that a sufficient contrast may be obtained through the accumulation of the particles at the concentration, the particles are each required to have the following performance: an $\epsilon$(Fe) of 580 or more. In addition, the molar absorption coefficient $\epsilon$ and the photoacoustic signal intensity are in a linear relationship, and hence the $\epsilon$(Fe) needs to be 580 or more for obtaining a necessary photoacoustic signal intensity. The ratio of the number of moles of the catechol-like compound to the number of moles of Fe needed for achieving an $\epsilon$(Fe) of 580 or more was estimated to be 270/10,000 or more from the graphs of FIG. 5A and FIG. 5B.

None of the particles B-3, B-4, and B-6 satisfied the condition that a ratio "catechol/Fe" should be 270/10,000 or more under which photoacoustic imaging was able to be performed.

Example 7

An amorphous particle A-9 containing dopamine as a catechol-like compound and a carboxydextran as a dispersion stabilizer was produced by the following method.

As in Example 2, an aqueous solution of dopamine ($9.5 \times 10^{-4}$ mol in terms of dopamine) and an aqueous solution of NaOH were added to an aqueous solution containing Fe$^{2+}$ and Fe$^{3+}$. 2 Milliliters of a 20-mg/ml aqueous solution of a carboxydextran (Meito Sangyo Co., Ltd.) were added to the aqueous solution. The resultant aqueous solution was formed into particles by being continuously mixed for 2 hours.

The particle size and the normalized photoacoustic signal PA(Fe) per iron amount were measured in the same manner as in Examples 1 and 2. The particle A-9 had a particle size of 12 nm and a normalized photoacoustic signal PA(Fe) per iron amount of $2.2 \times 10^{-4}$ (VJ$^{-1}$M$^{-1}$). The particle was able to be produced even when the carboxydextran was used as a dispersion stabilizer. Comparison between the particle A-2 produced by using the dextran as a dispersion stabilizer and the particle A-9 using the carboxydextran as a dispersion stabilizer showed that there were no large differences between the particles in particle size and normalized photoacoustic signal per iron amount.

Example 8

An amorphous particle A-10 containing dopamine as a catechol-like compound and an aminated PEG as a dispersion stabilizer was produced by the following method.

As in Example 3, dopamine and NaOH were added to an aqueous solution containing Fe$^{3+}$. 6.4 Milliliters of a 20-mg/ml aqueous solution of an aminated PEG (NOF CORPORATION, ME-200EA) were added to the aqueous solution. The resultant aqueous solution was formed into particles by being continuously mixed for 2 hours.

The particle size and the normalized photoacoustic signal PA(Fe) per iron amount were measured in the same manner as in Examples 1 and 2.

The particle A-10 had a particle size of 72 nm and a normalized photoacoustic signal PA(Fe) per iron amount of $2.9 \times 10^5$ (VJ$^{-1}$M$^{-1}$). The particle was able to be produced even when the aminated PEG was used as a dispersion stabilizer. Comparison between the particle A-6 produced by using the dextran as a dispersion stabilizer and the particle A-10 using the aminated PEG as a dispersion stabilizer showed that although there was a slight difference between the particles in particle size, there was no large difference between the particles in normalized photoacoustic signal per iron amount.

Example 9

Photoacoustic imaging was performed in vitro with the particle A-10 by the following method while bearing angiography in mind.

A solution containing the particle A-10 was prepared so that an Fe concentration in the solution became 608 µg/ml. The particle A-10 and blood collected from mice were blended at a ratio of 1:10 in terms of a volume ratio to provide a liquid "blood+particle A-10". The blending ratio was estimated on the assumption that 200 µl of the solution were intravenously injected into a mouse having a blood volume of 2 ml. For comparison, a liquid obtained by blending PBS and the blood at a ratio of 1:10 in terms of a volume ratio was referred to as "blood only", and a liquid obtained by blending the particle A-10 and PBS at a ratio of 1:10 in terms of a volume ratio was referred to as "particle A-10".

While bearing angiography in mind, each liquid was transferred to a polyethylene tube (IMAMURA Co., Ltd., outer diameter: 0.965 mm, inner diameter: 0.580 mm) and then photographing was performed with a photoacoustic imaging apparatus (Endra, Nexus 128). The photographing was performed at a wavelength of 680 nm. An image was obtained and a luminance was determined from the image.

Figure 6A:
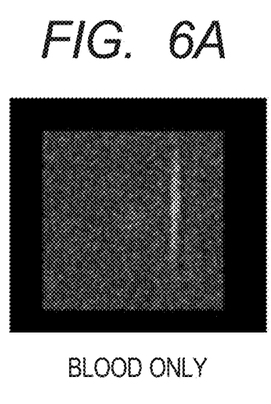
FIG. 6A is a photoacoustic imaging image of blood.
Figure 6B:
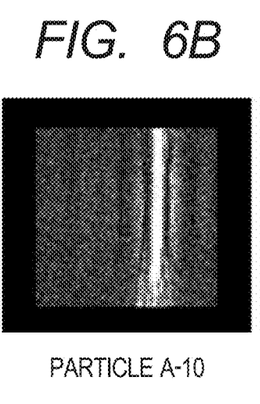
FIG. 6B is a photoacoustic imaging image of a solution containing a particle A-10.
Figure 6C:
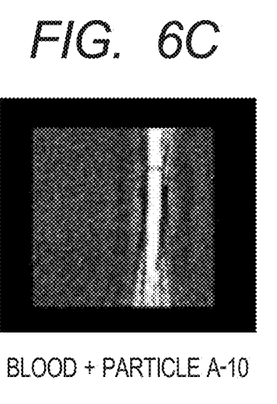
FIG. 6C is a photoacoustic imaging image of a solution containing the blood and the particle A-10.
Figure 6D:
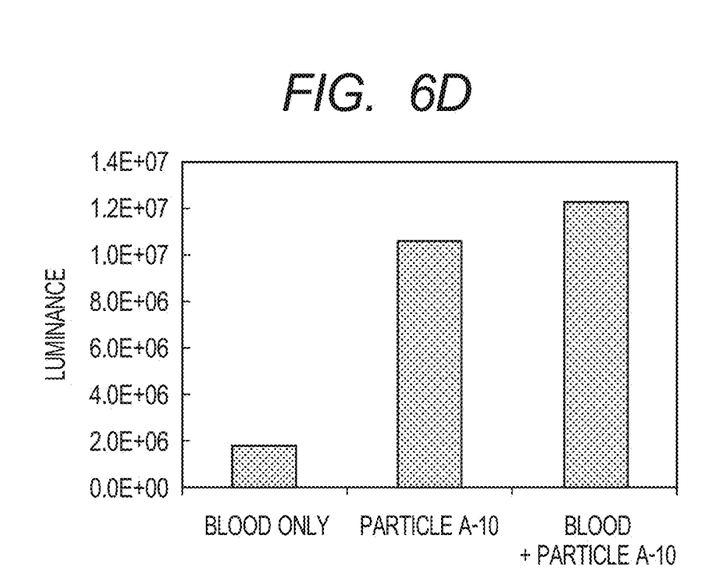
FIG. 6D shows the luminances of the blood, the solution containing the particle A-10, and the solution containing the blood and the particle A-10.

FIG. 6A is an image obtained in the liquid "blood only", FIG. 6B is an image obtained in the liquid "particle A-10", and FIG. 6C is an image obtained in the liquid "blood+ particle A-10". A clear tubular image was obtained in the liquid "blood+particle A-10" (FIG. 6C) as compared with the liquid "blood only" (FIG. 6A). FIG. 6D is a graph of luminances. The luminance of the liquid "blood+particle A-10" was 7.1 times as high as that of the liquid "blood only" and the luminance of the liquid "particle A-10" was 6.1 times as high as that of the liquid "blood only".

When 200 μl of the particle A-10 are intravenously injected into a mouse, the administration amount of Fe per body weight of the mouse is 6.08 mg/kg given that the body weight of the mouse is 20 g because the Fe concentration of the particle A-10 is 608 μg/ml. When the Resovist (trademark) is used as a contrast agent, the contrast agent can be administered in an amount of 0.45 mg/kg in terms of an Fe amount. An amount of 6.08 mg/kg is about 13.5 times as large as an amount of 0.45 mg/kg.

However, even when only 0.45 mg/kg of the particle A-10 was administered, the luminance was estimated to be 1.5 times as high as that of the blood according to the following calculation equation.

{(Luminance of particle A-10)/13.5+(luminance of blood only)}/(luminance of blood only)

In a paper (Chemical Reviews 2756-2782 (2010)), even when the luminance is only 1.65 times as high as that of the blood, a blurred vessel image changes into a clear vessel image on an image.

The foregoing showed that the particle of the present case was useful as a contrast agent when angiography was performed with a photoacoustic imaging apparatus.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application Nos. 2012-154471, filed Jul. 10, 2012, and 2013-041919, filed Mar. 4, 2013 which are hereby incorporated by reference herein in their entirety.

What is claimed is:

1. A contrast agent for photoacoustic imaging, comprising a particle,
    wherein the particle has dopamine and iron atoms, and
    wherein the particle has a ratio of a number of moles of the dopamine to a number of moles of the iron atoms that is from 270/10,000 to 3,000/10,000.

2. The contrast agent according to claim 1, wherein at least part of the iron atoms form a complex with a catechol-like compound.

3. The contrast agent according to claim 1, further comprising oxygen atoms, wherein at least part of the iron atoms are bonded to the oxygen atoms.

4. The contrast agent according to claim 1, wherein the particle is amorphous.

5. The contrast agent according to claim 1, wherein the particle absorbs light in a near infrared region.

6. The contrast agent according to claim 1, wherein an average particle size is 1 nm to 5,000 nm.

7. The contrast agent according to claim 1, further comprising a dispersion stabilizer.

8. The contrast agent according to claim 7, wherein the dispersion stabilizer is selected from the group consisting of a sugar and derivatives thereof.

9. The contrast agent according to claim 7, wherein the dispersion stabilizer comprises at least one selected from the group consisting of a dextran, a carboxydextran, an aminated dextran, a pullulan, and a polyethylene glycol.

10. A contrast agent for photoacoustic imaging, comprising a particle,
    wherein the particle has dopamine and iron atoms, and
    wherein a molar absorption coefficient per iron amount of the particle is 580 or more.

* * * * *